(12) United States Patent
Lin et al.

(10) Patent No.: US 9,019,494 B2
(45) Date of Patent: Apr. 28, 2015

(54) SURFACE-ENHANCED RAMAN SCATTERING SUBSTRATE AND A TRACE DETECTION METHOD OF A BIOLOGICAL AND CHEMICAL ANALYTE USING THE SAME

(75) Inventors: Ding-Zheng Lin, Taipei (TW); Yi-Ping Chen, Kaohsiung (TW); Tsung-Dar Cheng, Taipei (TW); I-Ling Kao, Taipei (TW); Ping-Chen Chen, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 199 days.

(21) Appl. No.: 13/399,953

(22) Filed: Feb. 17, 2012

(65) Prior Publication Data

US 2013/0038870 A1 Feb. 14, 2013

Related U.S. Application Data

(60) Provisional application No. 61/523,398, filed on Aug. 14, 2011.

(30) Foreign Application Priority Data

Nov. 7, 2011 (TW) .............................. 100140479 A (51) Int. Cl.
*G01J 3/44* (2006.01)
*G01N 21/65* (2006.01)

(52) U.S. Cl.
CPC .................................. *G01N 21/658* (2013.01)

(58) Field of Classification Search
CPC .......................................................... G01J 3/44
USPC .............................................. 356/301, 72–73
See application file for complete search history.

(56) References Cited

U.S. PATENT DOCUMENTS

| 7,242,470 | B2 * | 7/2007 | Cullum et al. ................. 356/301 |
| 7,371,457 | B2 | 5/2008 | Oldenburg et al. |
| 7,453,565 | B2 | 11/2008 | Wang et al. |
| 7,460,224 | B2 | 12/2008 | Wang et al. |
| 7,864,313 | B2 | 1/2011 | Baumberg et al. |
| 2002/0182716 | A1 * | 12/2002 | Weisbuch et al. ........... 435/287.2 |
| 2005/0123442 | A1 * | 6/2005 | Gu et al. .......................... 422/57 |
| 2011/0109902 | A1 * | 5/2011 | Lin et al. ....................... 356/301 |

FOREIGN PATENT DOCUMENTS

| TW | 200728706 | 8/2007 |
| TW | 201111769 | 4/2011 |
| TW | 201116819 | 5/2011 |

OTHER PUBLICATIONS

Nancy J. Azabo et al., "Surface-Enhanced Raman Scattering from an Etched Polymer Substrate," Analytical Chemistry, Jul. 1, 1997, pp. 2418-2425, vol. 69, No. 13, American Chemical Society, US.

(Continued)

*Primary Examiner* — Abdullahi Nur (57) ABSTRACT

The invention provides a surface-enhanced Raman scattering substrate and a trace detection method of a biological and chemical analyte using the same. The substrate includes: a substrate having a periodic nanostructure; a reflection layer formed on the substrate; a dielectric layer formed on the reflection layer; and a metal thin film layer formed on the dielectric layer.

25 Claims, 8 Drawing Sheets

(56) References Cited

OTHER PUBLICATIONS

Matthias Geissler et al., "Plastic Substrates for Surface-Enhanced Raman Scattering," J. Phys. Chem., 2009. pp. 17296-17300, vol. 113, American Chemical Society, US.

Charles J Choi et al., "Surface-Enhanced Raman Nanodomes," Nanotechnology, 2010, pp. 1-7, vol. 21, IOP Publishing, US.

R.P. Van Duyne et al., "Atomic Force Microscopy and Surface-Enhanced Raman Spectroscopy-I. Ag Island Films and Ag Film over Polymer Nanosphere Surfaces Supported on Glass," J. Chem. Phys. Aug. 1, 1993, pp. 2101-2115, vol. 99, American Institute of Physics, US.

D. Z. Lin et al., "Optimizing Electromagnetic Enhancement of Flexible Nano-Imprinted Hexagonally Patterned Surface-Enhanced Raman Scattering Substrates," Feb. 28, 2011, pp. 4337-4345, vol. 19, No. 5, Optics Express, US.

Taiwan Patent Office, Office Action, Patent Application Serial No. 100140479, Jun. 11, 2014, Taiwan.

* cited by examiner

SURFACE-ENHANCED RAMAN SCATTERING SUBSTRATE AND A TRACE DETECTION METHOD OF A BIOLOGICAL AND CHEMICAL ANALYTE USING THE SAME

CROSS REFERENCE TO RELATED APPLICATIONS

This application claims the benefit of U.S. Provisional Application No. 61/523,398, filed on Aug. 14, 2011, the entirety of which is/are incorporated by reference herein. This Application claims priority of Taiwan Patent Application No. 100140479, filed on Nov. 7, 2011, the entirety of which is incorporated by reference herein.

BACKGROUND OF THE INVENTION

1. Field of the Invention

The present invention relates to a substrate, and in particular relates to a surface-enhanced Raman scattering substrate and a trace detection method of a biological and chemical analyte using the same.

2. Description of the Related Art

There are several poisonous chemical pollutants in the environment, and these pollutants have different maximum allowable concentrations, e.g. benze (5.1 ppb), Pb (50 ppb), Cd (5 ppb), paraquat (20 ppb), 1,1,1-trichloroethane (0.2 ppm). However, traditional detection instruments are expensive and take a lot of time for measurements, thereby limiting its time-effectiveness and popularity. Therefore, those skilled in the art are devoted to develop a highly sensitive, rapid and low cost trace detection device to analyze biological and chemical analytes.

A Raman Scattering Spectrum has the advantages of fingerprint specificity and multi-domain applications, and thus it is applied to trace detection. However, the Raman scattering intensity is very weak. Scientists use a metal structure to induce the surface-Enhanced Raman Scattering (SERS) to amplify the scattering intensity $10^4$-$10^{12}$ times.

The U.S. Pat. No. 7,242,470 discloses a nanostructure formed on a substrate. The nanostructure in the form of nanosphere is arranged self-assembly on the substrate. However, the adhesion between the nanostructure and the substrate is poor, and the nanostructure is not a continuous film. Thus, fabricating such SERS substrate having a large area, high uniformity and high Raman scattering intensity is a challenge.

The U.S. Pat. No. 7,864,313 discloses a substrate. A photonic crystal structure and a Bragg reflector are formed on the substrate to enhance the Raman scattering intensity of the analytes approaching the substrate. However, the substrate is formed by a photo lithography process, a physical etching process or chemical etching process, and these processes are expensive and time consuming.

Accordingly, there is a need to develop a large area, inexpensive SERS substrate, and the substrate also has a high Raman scattering intensity for trace analysis application.

BRIEF SUMMARY OF THE INVENTION

The invention provides a surface-enhanced Raman scattering substrate and a trace detection method of a biological and chemical analyte using the same. The substrate includes: a substrate having a periodic nanostructure; a reflection layer formed on the substrate; a dielectric layer formed on the reflection layer; and a metal thin film layer formed on the dielectric layer.

The invention also provides a trace detection method of a biological and chemical analyte, comprising: providing the surface-enhanced Raman scattering substrate to absorb an analyte; and providing a laser excitation light to the analyte to form a Raman scattering signal.

A detailed description is given in the following embodiments with reference to the accompanying drawings.

BRIEF DESCRIPTION OF THE DRAWING

For a more complete understanding of the present invention, and the advantages thereof, reference is now made to the following descriptions taken in conjunction with the accompanying drawings, in which.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
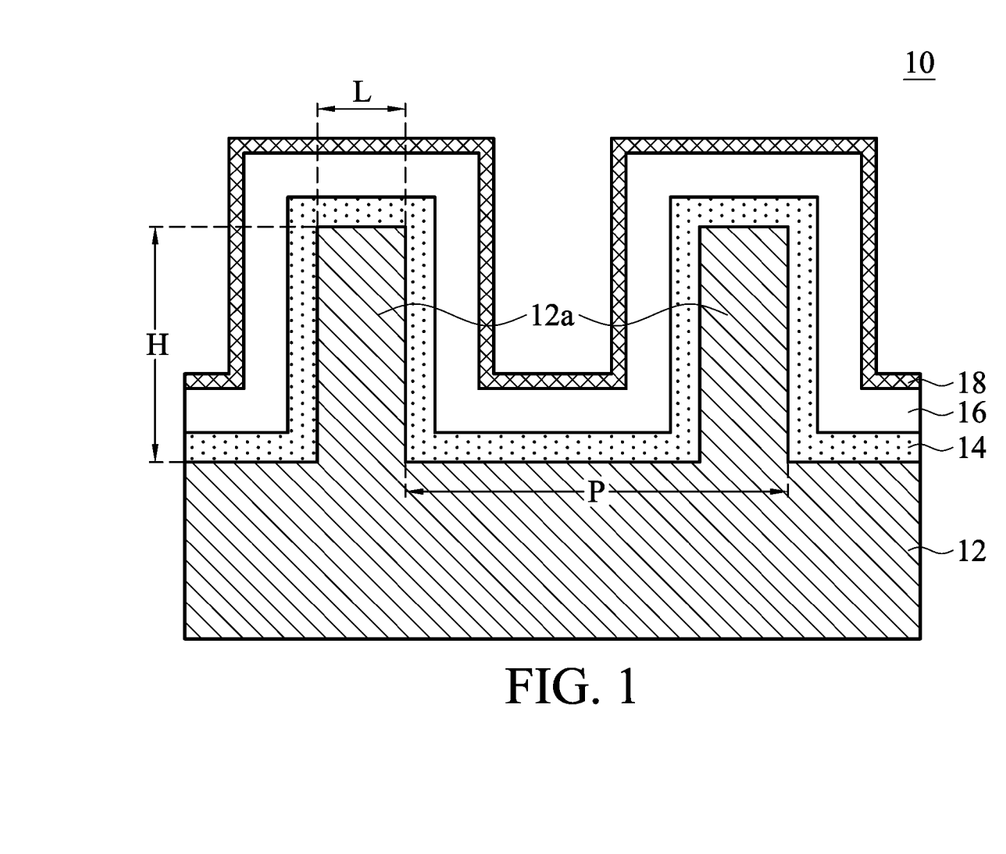
FIG. 1 shows a cross-sectional schematic representation of a surface-enhanced Raman scattering substrate in accordance with an embodiment of the invention.

FIG. 1 shows a cross-sectional schematic representation of a surface-enhanced Raman scattering (SERS) substrate 10 of the invention. A reflection layer 14, a dielectric layer 16, and a metal thin film layer 18 are sequentially formed on the substrate 12. The substrate 12 comprises metal, inorganic material, organic polymer material or combinations thereof. Note that the substrate 12 has a periodic nanostructure 12a, and the substrate 12 and the periodic nanostructure 12a are formed by the same or different material. In other words, the substrate 12 and the periodic nanostructure 12a may be formed by one step or two steps.

The periodic nanostructure 12a has a shape of a cylinder, semi-ball, sine wave, triangle, disk or combinations thereof. However, the shape is not limited to the above-mentioned shapes. Those skilled in the art may change the shape of the periodic nanostructure 12a according to actual applications. The periodic nanostructure 12a may be formed by a nanoimprint process or nano electroforming process.

The periodic nanostructure 12a has a period of 10-1000 nm, and preferably 300-700 nm which is a better choice for a visible wavelength laser. If the period P is too small, the process thereof is difficult or even impossible. If the period P is too large, the substrate resonance condition will not match with the incident laser wavelength.

The periodic nanostructure 12a has a duty cycle (L/P) of 0.1-0.9. If the ratio L/P is too large, the nanoimprint process is difficult. If the ratio L/P is too small, it cannot efficiently improve the plasmon resonance on the surface-enhanced Raman scattering substrate and the Raman signal of the analyte.

The periodic nanostructure 12a has a height to width ratio (H/L, aspect ratio) about 0.1-3, and preferably 0.5-2. If the aspect ratio is too low, the nanostructure is too flat to obtain the excitation of the surface plasmon resonance. If the aspect ratio is too high, the process difficulty of the nanoimprint process or nano electroforming process will be largely increased.

The reflection layer 14 is conformally formed on the substrate 12 having the periodic nanostructure 12a. The function of the reflection layer 14 is to shield the substrate 12 from interference from self-absorption and Raman background signal. Thus, the thickness of the reflection layer 14 is larger than a skin depth of the material of the reflection layer 14 at the operation laser wavelength.

The reflection layer 14 has a reflection of about larger than 70%, and preferably 85%. The reflection layer 14 comprises metal, alloy comprising thereof or dielectric material, and the metal comprises Ag, Al, Au, Cu, Rh or Pt, the alloy comprises Cu—Al alloy or Au—Ni alloy, and the dielectric material comprises silicon, germanium or the like.

The function of the dielectric layer 16 is to adjust the resonance wavelength of the Fabry-Perot resonator. The dielectric layer comprises a material having a refractive index of 1.3-5.0 and comprises silicon dioxide (n=1.5), aluminum oxide (n=1.77), silicon nitride (n=2), titanium oxide (n=2.9) or silicon (n=4).

The function of the metal thin film layer 18 is to excite the surface plasmon resonance. In order to adjust the resonance wavelength of the surface plasmon and couple the surface plasmon resonance mode (SP mode) with Fabry-Perot resonance mode (FP mode), the thickness of the metal thin film layer 18 is smaller than a skin depth of the material of the metal thin film layer 18 at the operation laser wavelength. Therefore, the two interfaces between the metal thin film layer 18 and the dielectric layer 16 may be coupled to each other to produce a new resonance mode, which can also adjust the resonance wavelength of the SERS substrate.

Note that the metal thin film layer 18 is a continuous film or non-continuous film. In one embodiment, the metal thin film layer 18 is preferably a continuous film to improve the Raman scattering signal.

The metal thin film layer 18 has a thickness of smaller than 50 nm, and the thickness of the metal thin film layer 18 is smaller than that of the reflection layer 14. The metal thin film layer 18 comprises Au, Ag, Pt, Fe, Co, Ni, Cu, Al, Cr or combinations thereof.

From the above description, the Raman scattering signal is improved by the multi-layers (comprising substrate 12 having the periodic nanostructure 12a, reflection layer 14, dielectric layer 16 and metal thin film layer 18) of the surface-enhanced Raman scattering substrate 10. Each layer of the multi-layers has a specific function. Therefore, the Raman scattering signal is improved by adjusting the aspect ratio and period of the periodic nanostructure 12a, or adjusting the thickness of the multi-layers to make the resonance wavelength of the surface plasmon coincide with the wavelength of excitation laser or wavelength of the Raman scattering.

Additionally, the invention also provides a trace detection method of a biological and chemical analyte using the surface-enhanced Raman scattering substrate 10. The method comprises a surface-enhanced Raman scattering substrate 10 being provided to absorb an analyte. Also, the excitation laser (with wavelength of 400 nm-1200 nm) is provided to the analyte to form a Raman scattering signal. The excitation laser comprises a solid state laser having a wavelength of 355 nm, 532 nm, or 1064 nm, a gas laser having a wavelength of 488 nm, 514.5 nm or 632.8 nm, or a semiconductor laser having a wavelength of 405 nm, 532 nm, 635 nm, 670 nm, 780 nm, 808 nm or 1064 nm.

The surface-enhanced Raman scattering substrate 10 may be used to detect the analyte of a solid, gas or liquid phase. The pH value of analyte in liquid phase is in the range of pH 2-12. When the analyte is in medium of water or organic solvent, the analyte concentration is about 100 ppm-0.1 ppb. When the analyte is in the medium of air, the analyte concentration is about 1000 ppm-1 ppb.

In one embodiment, the detection limit of the Malachite Green solution is $10^{-10}$ M (about 0.1 ppb).

Furthermore, an electrical field and/or a magnetic field may be applied to the surface-enhanced Raman scattering substrate 10 to enhance the Raman scattering signal.

Moreover, the thickness of the metal thin film layer 18 and/or the dielectric layer 16 may be tuned to enhance the Raman scattering signal.

EXAMPLE

Examples 1-6 the Effect of the Reflection Layer

Figure 2:
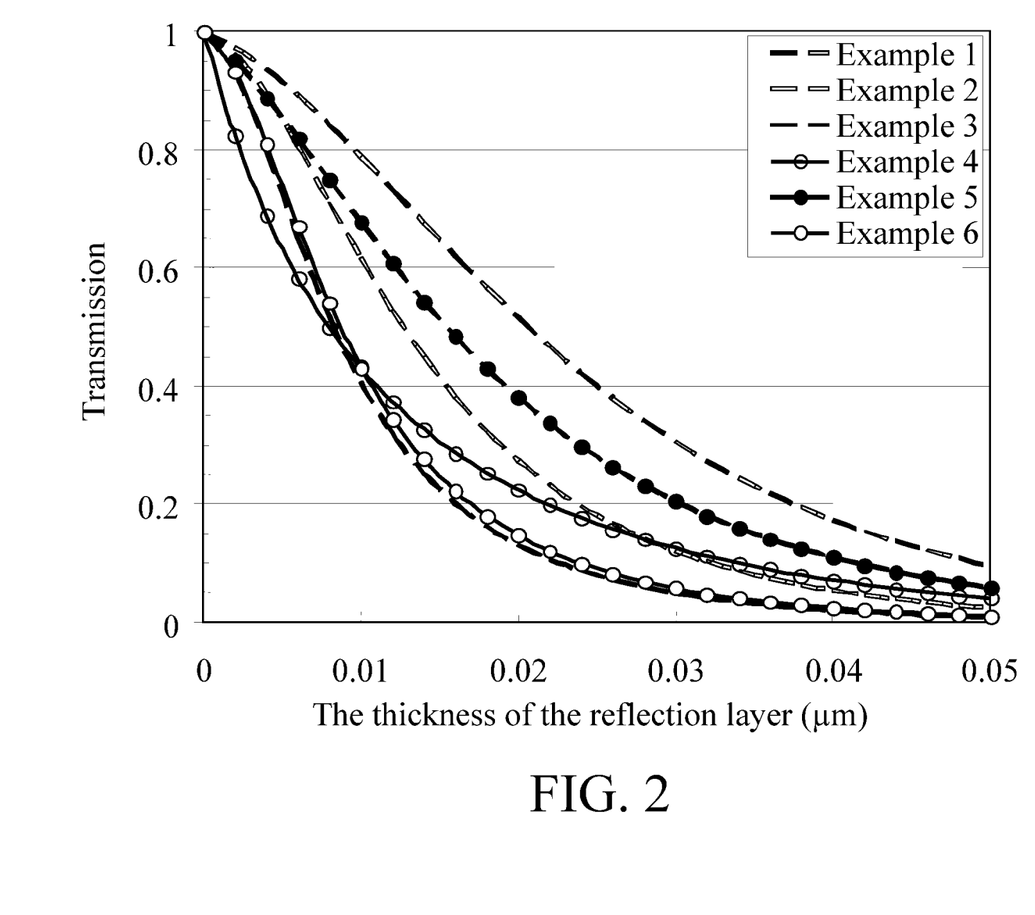
FIG. 2 is a schematic viewing showing the thickness of the reflection layer versus the transmission of the Example of the invention.

Table 1 shows the structure of the Examples 1-6 (the transmission of the metal thin film layer (Ag thin film or Au thin film) coated on the plastic substrate at a wavelength of 400 nm, 550 nm or 785 nm is measured). FIG. 2 is a schematic viewing showing the thickness of the reflection layer of the Examples 1-6 versus transmission. As shown in FIG. 2, the transmission is decreased with the increase in the thickness of the reflection layer. Referring to Example 6, when the Au film layer is larger than 30 nm, the transmission of 785 nm Laser is smaller than 7%.

Figure 3:
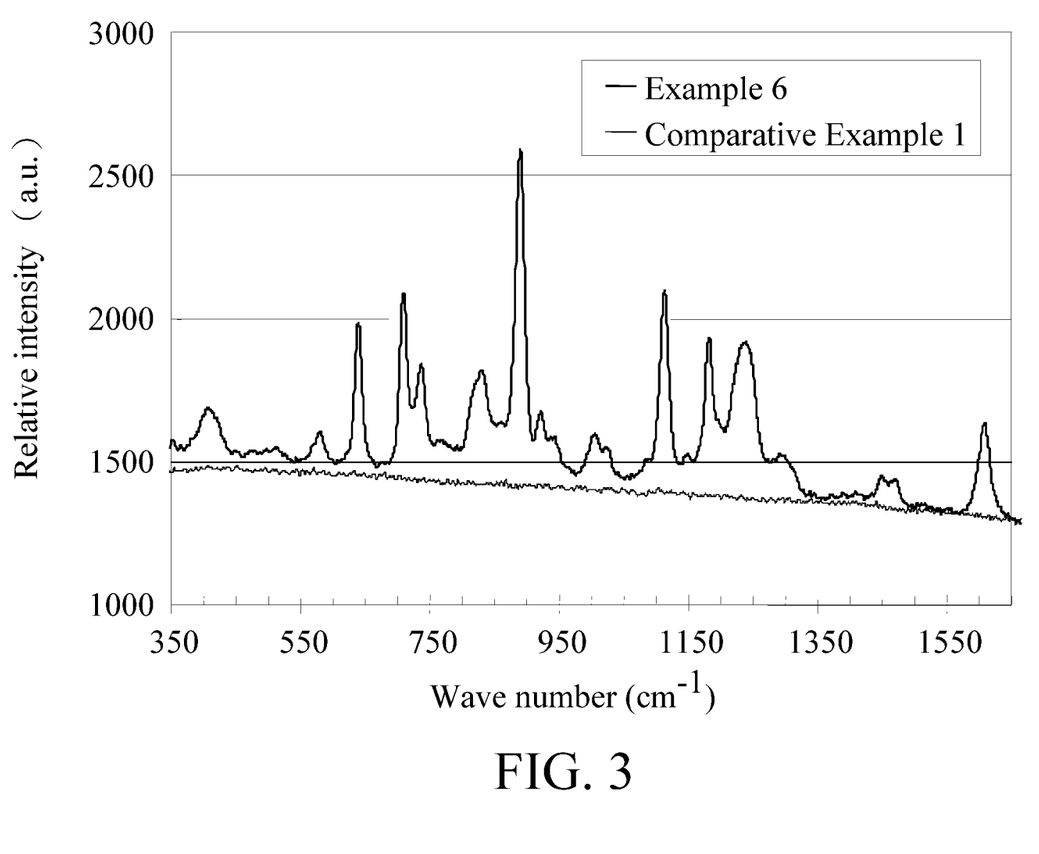
FIG. 3 is a graph of Raman spectra showing the shielding difference between the Comparative Example 1 and Example 6 with a reflection layer.

FIG. 3 is a graph of Raman spectra under 785 nm excitation showing the Raman signal of Example 6 (plastic substrate+50 nm Ag) and Comparative Example 1 (only plastic substrate). As shown in FIG. 3, compared with the Comparative Example 1, Example 6 has a flat Raman background signal. Thus, the reflection layer indeed has a shielding effect to prevent the background signal of the substrate from interfering with the detection of the analyte.

TABLE 1

| Example | structure | Laser excitation wavelength (nm) |
|---|---|---|
| Example 1 | Substrate + Ag layer | 400 |
| Example 2 | Substrate + Ag layer | 550 |
| Example 3 | Substrate + Ag layer | 785 |
| Example 4 | Substrate + Au layer | 400 |
| Example 5 | Substrate + Au layer | 550 |
| Example 6 | Substrate + Au layer | 785 |

Examples 7-9 the Effect of the Dielectric Layer

Figure 4:
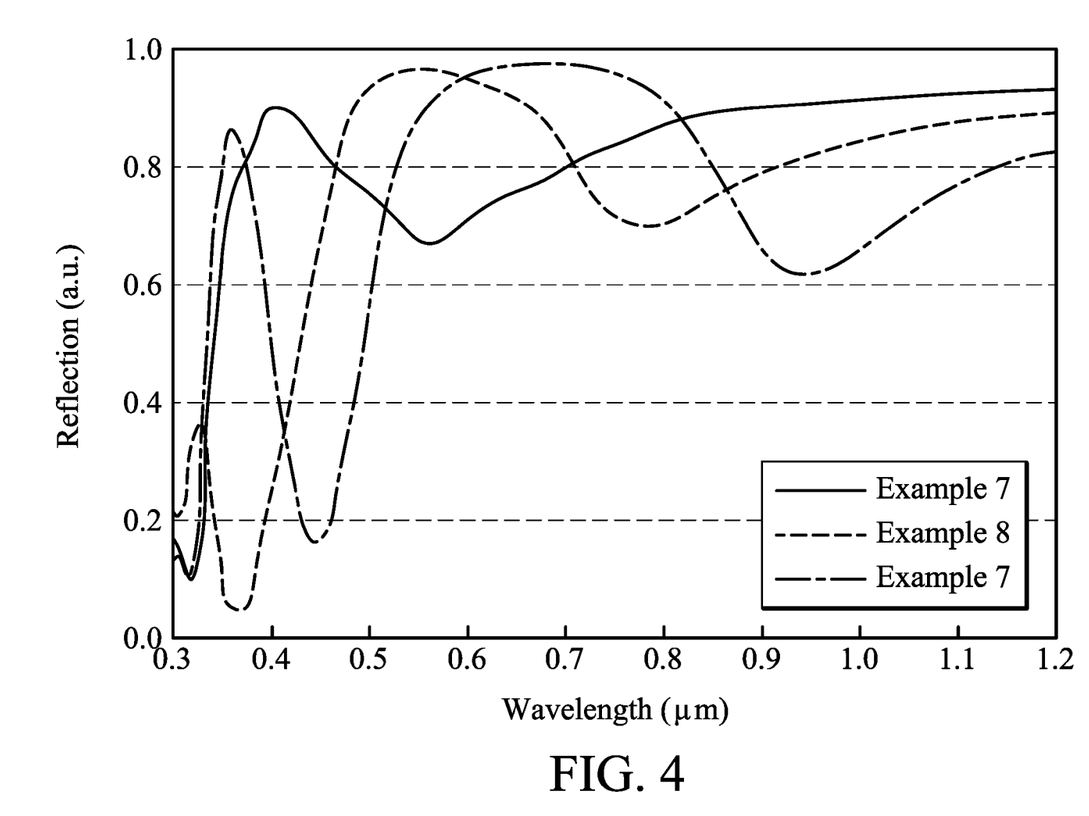
FIG. 4 is a graph showing reflection spectrum of the Example 7-9 of the invention.

Table 2 shows the structure of the Examples 7-9 (the reflection layer, the dielectric layer and the metal thin film are sequential formed on the substrate). FIG. 4 is a graph showing reflection spectrum of Examples 7-9 and showing how the thickness of the dielectric layer affects the resonance wavelength of the Fabry-Perot resonance mode. As shown in FIG. 4, the resonance wavelength undergoes a red shift, when the thickness of the dielectric layer is increased. Therefore, the resonance wavelength of the Fabry-Perot resonator may be adjusted by changing the thickness of the dielectric layer.

TABLE 2

| Example | structure |
| --- | --- |
| Example 7 | Substrate + 35 nm Ag layer + 100 nm $SiO_2$ + 5 nm Au thin film layer |
| Example 8 | Substrate + 35 nm Ag layer + 150 nm $SiO_2$ + 5 nm Au thin film layer |
| Example 9 | Substrate + 35 nm Ag layer + 200 nm $SiO_2$ + 5 nm Au thin film layer |

Examples 10-14 Effect of the Metal Thin Film Layer

Figure 5:
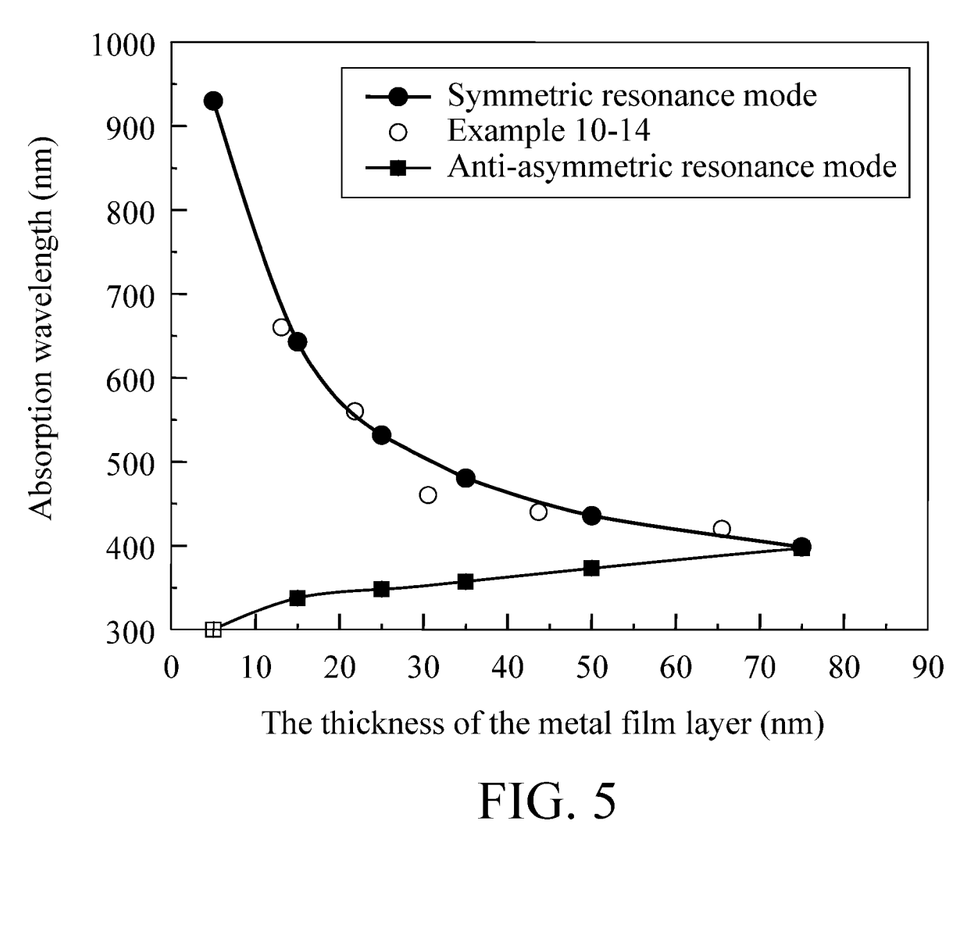
FIG. 5 is a schematic viewing showing the thickness of the metal thin film layer versus absorption wavelength of the invention.

Table 3 shows the structure the Examples 10-14. The structure has the periodic nanostructure substrate (period of 300 nm, height of 100 nm) and an Ag film layer. FIG. 5 is a schematic viewing showing the thickness of the metal thin film layer versus absorption wavelength (also called surface plasmon resonance wavelength) of the Examples 10-14. As shown in FIG. 5, when the thickness of the metal thin film layer is smaller than 75 nm, the surface plasmon at two interfaces of the metal/dielectric layer and metal/air may be coupled to each other to produce a symmetric resonance mode and an anti-asymmetric resonance mode. The wavelength of the symmetric resonance mode is red-shifted with the decrease of the thickness of the metal thin film, and the wavelength of the anti-symmetric resonance mode is blue-shifted with the decrease of the thickness of the metal thin film.

TABLE 3

| Example | structure |
| --- | --- |
| Example 10 | the periodic nanostructure substrate + 15 nm Ag thin film layer |
| Example 11 | the periodic nanostructure substrate + 25 nm Ag thin film layer |
| Example 12 | the periodic nanostructure substrate + 35 nm Ag thin film layer |
| Example 13 | the periodic nanostructure substrate + 50 nm Ag thin film layer |
| Example 14 | the periodic nanostructure substrate + 75 nm Ag thin film layer |

Example 15

Example 15 has a structure as follows: the reflection layer (35 nm of Ag layer), the dielectric layer (200 nm of $SiO_2$ layer), and the metal thin film layer (10 nm of Ag film) are sequentially formed on a substrate having the periodic nanostructure (period=400 nm, height=240 nm).

Comparative Example 2 has a structure as follows: the reflection layer (35 nm of Au layer), the dielectric layer (200 nm of $SiO_2$ layer), and the metal thin film layer (10 nm of Ag thin film layer) are sequential formed on a flat substrate.

Figure 6:
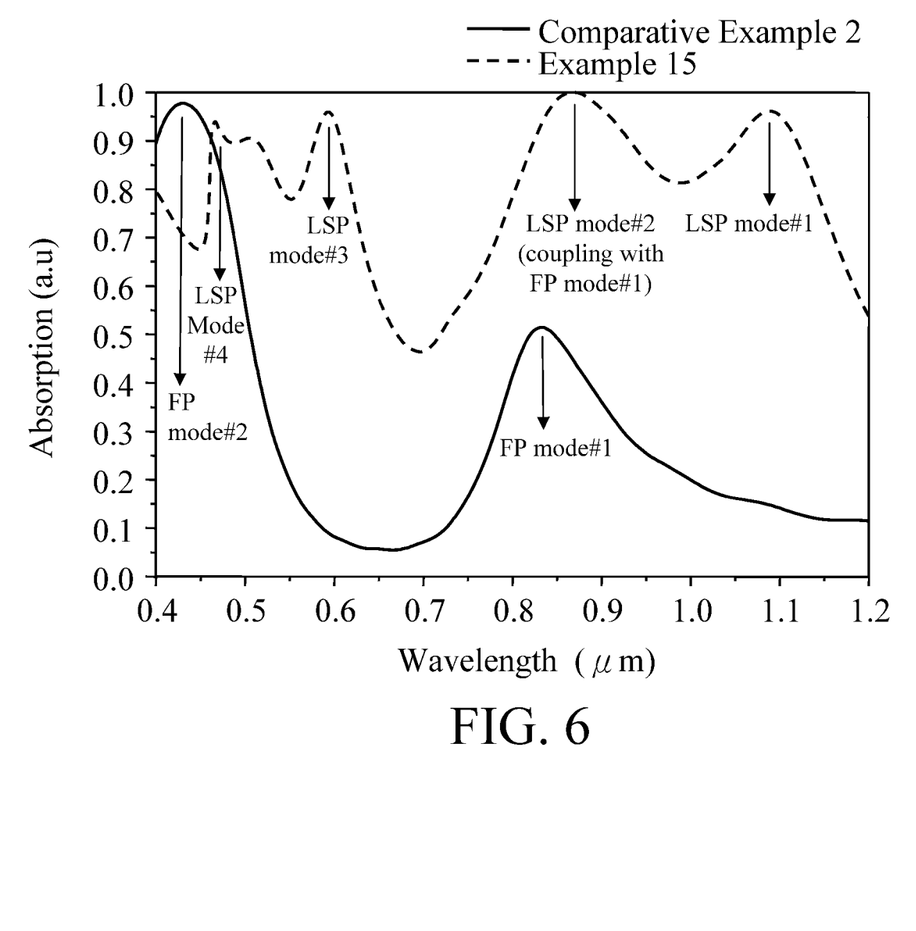
FIG. 6 is a graph showing absorption spectrum of the Example with a periodic nanostructure and Comparative Example with a flat structure.

FIG. 6 is a graph showing absorption spectrum of the Example 15 and Comparative Example 2. As shown in FIG. 6, the Fabry-Perot resonator of Comparative Example 2 has two peaks of 830 nm and 430 nm individually corresponding to the FP mode#1 and FP mode#2. When the Fabry-Perot resonator is formed on the substrate having the periodic nanostructure (Example 15), the absorption spectrum becomes more complicated because the probability of the Localized Surface Plasmon mode (LSP) is increased caused by the periodic nanostructure. The peak wavelength of 860 nm is the coupling result between the LSP mode and FP mode. Therefore, more and more laser excitation lights are focused on the periodic nanostructure to form a hot spot.

Figure 7:
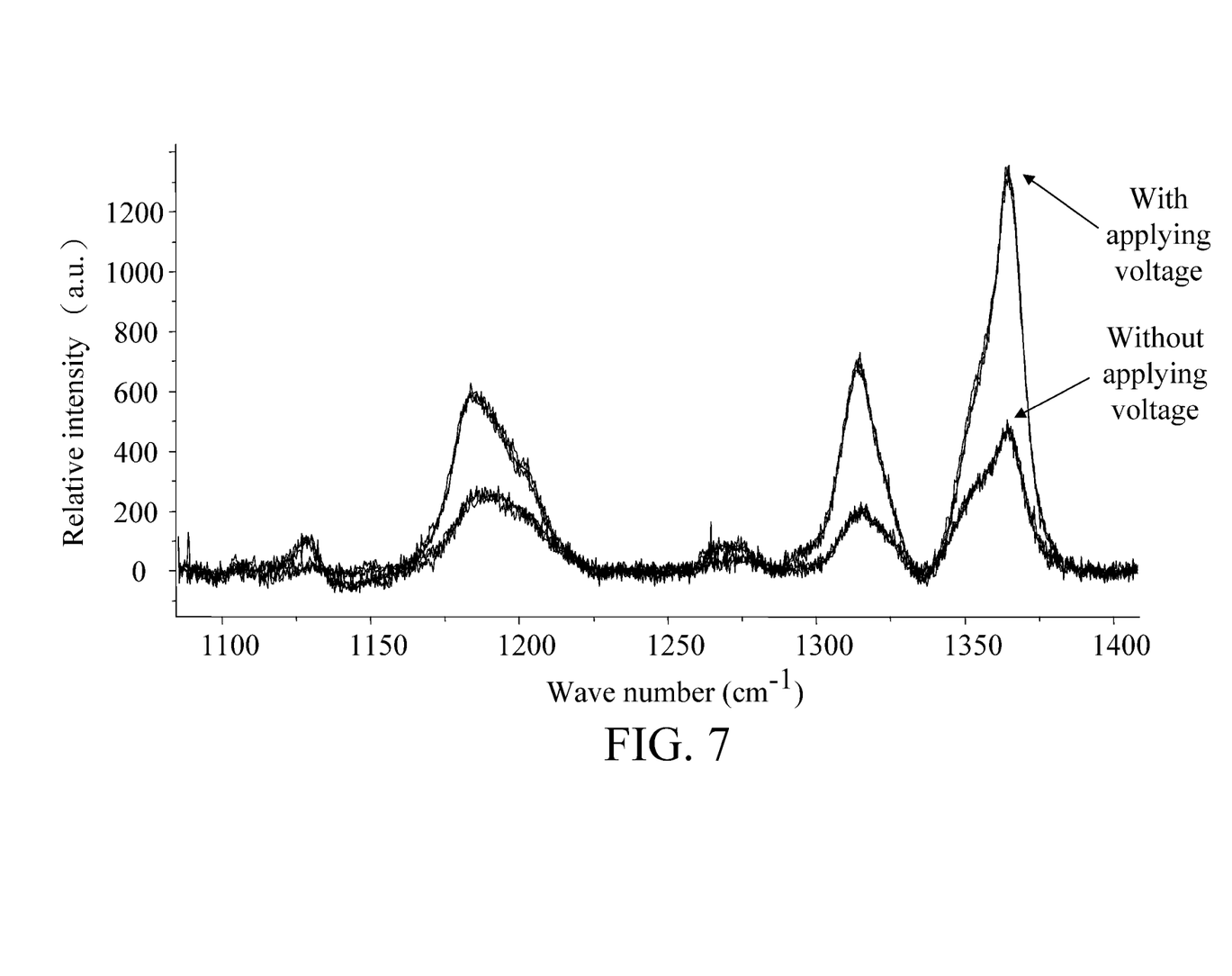
FIG. 7 is a graph showing Raman spectra of the Example 15 with or without applying voltage by detecting the Rhodamine 6G solution.

FIG. 7 is a graph showing Raman spectra of the Example 15 by detecting the $10^{-4}$ M Rhodamine 6G solution. As shown in FIG. 7, compared with and without voltage being applied, the Raman signal is improved by applying voltage (−1 V). Because the voltage may attract the ionic analyte to move to the substrate, the Raman scattering signal is improved.

Comparative Example 3 is a commercial SERS substrate (Klarite), Comparative Example 4 is a commercial SERS substrate (NIDEK, nanorods formed on the substrate), and Comparative Example 5 is a flat Au layer formed on the substrate.

Figure 8:
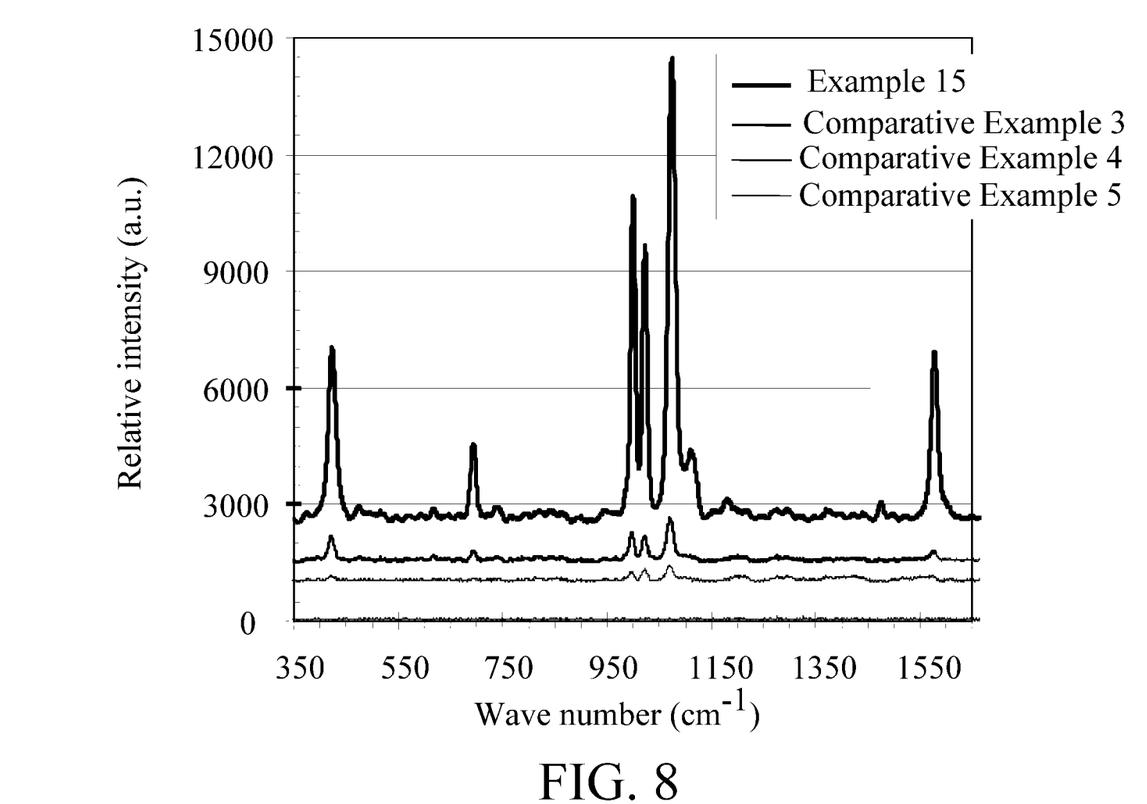
FIG. 8 is a graph showing Raman spectra of the Example and Comparative Example by detecting a thiophenol monolayer.

FIG. 8 is a graph showing Raman spectra of the Example 15 and Comparative Examples 3-5 by detecting a thiophenol monolayer (by using a 785 nm excitation laser).

As shown in FIG. 8, the Raman scattering signal of Example 15 is more than 10 times comparing with Comparative Example 3-5. Thus, the Raman scattering signal is improved by the multi-layers of the surface-enhanced Raman scattering substrate, comprising the substrate having the periodic nanostructure, the reflection layer, the dielectric layer and the metal thin film layer.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A surface-enhanced Raman scattering substrate, comprising:
    a substrate having a periodic nanostructure, wherein the periodic nanostructure is formed in one piece with the substrate;
    a reflection layer formed on the substrate, wherein the reflection layer is a separately formed structure disposed on a surface of the substrate;
    a dielectric layer formed on the reflection layer; and
    a metal thin film layer formed on the dielectric layer.

2. The surface-enhanced Raman scattering substrate as claimed in claim 1, wherein the substrate having the periodic nanostructure comprises metal, inorganic material, organic polymer material or combinations thereof.

3. The surface-enhanced Raman scattering substrate as claimed in claim 1, wherein the periodic nanostructure and the substrate are formed by the same material.

4. The surface-enhanced Raman scattering substrate as claimed in claim 1, wherein the periodic nanostructure has a shape of a cylinder, semi-ball, sine wave, triangle, disk or combinations thereof.

5. The surface-enhanced Raman scattering substrate as claimed in claim 1, wherein the periodic nanostructure has a period of 10-1000 nm.

6. The surface-enhanced Raman scattering substrate as claimed in claim 1, wherein the periodic nanostructure has a duty cycle of 0.1-0.9.

7. The surface-enhanced Raman scattering substrate as claimed in claim 1, wherein the periodic nanostructure has an aspect ratio about 0.1-3.

8. The surface-enhanced Raman scattering substrate as claimed in claim 1, wherein the reflection layer has a reflection of about larger than 70%.

9. The surface-enhanced Raman scattering substrate as claimed in claim 1, wherein the reflection layer comprises metal, alloy comprising thereof or dielectric material.

10. The surface-enhanced Raman scattering substrate as claimed in claim 9, wherein the metal comprises Ag, Al, Au, Cu, Rh or Pt.

11. The surface-enhanced Raman scattering substrate as claimed in claim 1, wherein the dielectric layer comprises a material having a refractive index of 1.3-5.0.

12. The surface-enhanced Raman scattering substrate as claimed in claim 1, wherein the dielectric layer comprises silicon dioxide (n=1.5), aluminum oxide (n=1.77), silicon nitride (n=2), titanium oxide (n=2.9) or silicon (n=4).

13. The surface-enhanced Raman scattering substrate as claimed in claim 1, wherein the metal thin film layer has a thickness of smaller than 50 nm.

14. The surface-enhanced Raman scattering substrate as claimed in claim 1, wherein the thickness of the metal thin film layer is smaller than that of the reflection layer.

15. The surface-enhanced Raman scattering substrate as claimed in claim 1, wherein the metal thin film layer has a continuous or non-continuous structure.

16. The surface-enhanced Raman scattering substrate as claimed in claim 1, wherein the metal thin film layer comprises Au, Ag, Pt, Fe, Co, Ni, Cu, Al, Cr or combinations thereof.

17. A trace detection method of a biological and chemical analyte, comprising:

providing the surface-enhanced Raman scattering substrate as claimed in claim 1 to absorb an analyte; and
providing a laser excitation light to the analyte to form a Raman scattering signal.

18. The trace detection method of a biological and chemical analyte as claimed in claim 17, further comprising:
applying an electrical field and/or a magnetic field to the metal thin film layer to enhance the Raman scattering signal.

19. The trace detection method of a biological and chemical analyte as claimed in claim 17, wherein the analyte is in a medium of pH 2-12 solution.

20. The trace detection method of a biological and chemical analyte as claimed in claim 17, wherein the analyte is in the medium of water or organic solvent, and the analyte concentration in the medium is about 100 ppm-0.1 ppb.

21. The trace detection method of a biological and chemical analyte as claimed in claim 17, wherein the analyte is in the medium of air, and the analyte concentration in the medium is about 1000 ppm-1 ppb.

22. The trace detection method of a biological and chemical analyte as claimed in claim 17, further comprising tuning the thickness of the metal thin film layer and/or the dielectric layer to enhance the Raman scattering signal.

23. The surface-enhanced Raman scattering substrate as claimed in claim 1, wherein the reflection layer, dielectric layer, and metal thin film layer are conformal to the periodic nanostructure.

24. The surface-enhanced Raman scattering substrate as claimed in claim 1, wherein the dielectric layer is formed directly on the reflection layer.

25. The surface-enhanced Raman scattering substrate as claimed in claim 1, wherein the substrate and the reflection layer are formed from different materials.

* * * * *